United States Patent [19]

Choy

[11] Patent Number: 4,685,446
[45] Date of Patent: Aug. 11, 1987

[54] METHOD FOR USING A VENTRICULAR ASSIST DEVICE

[76] Inventor: Daniel S. J. Choy, 892 Riverbank Rd., Stamford, Conn. 06903

[21] Appl. No.: 582,118

[22] Filed: Feb. 21, 1984

[51] Int. Cl.⁴ .................................................. A61M 29/02
[52] U.S. Cl. ...................................... 128/1 D; 604/99
[58] Field of Search .............................. 128/1 D, 64; 604/96–103

[56] References Cited

U.S. PATENT DOCUMENTS

| | | | |
|---|---|---|---|
| 4,154,227 | 5/1979 | Kraus et al. | 128/1 D |
| 4,245,622 | 1/1981 | Hutchins, IV | 128/1 D |
| 4,439,186 | 3/1984 | Kuhl | 128/1 D |
| 4,448,190 | 5/1984 | Freeman | 128/1 D |
| 4,453,537 | 6/1984 | Spitzer | 128/1 D |

FOREIGN PATENT DOCUMENTS 2233293  1/1973  Fed. Rep. of Germany ..... 128/1 D

OTHER PUBLICATIONS

D. Bregman, E. N. Parodi, and J. R. Malm, "Left Ventricular and Unidirectional Intra-Aortic Balloon Pumping", *Journal of Thoracic and Cardiovascular Surgery*, vol. 68, No. 5, Nov. 1974, pp. 677–686.

D. E. Donald and D. C. McGoon, "Circulatory Support by a Left Ventricular Balloon Pump," Supp. 1 to *Circulation*, vols. XLIII and XLIV.

H. T. Dodge, et al., "Usefulness and Limitations of Radiographic Methods for Determining Left Ventricular Volume," *Am. Journal of Card.*, vol. 18, pp. 10–24.

J. Ross, Jr., et al., "The Architecture of the Heart in Systole and Diastole," *Circulation Research*, vol. XXI, Oct. 1967, pp. 409–421.

H. Arvidsson, "Angiocardiographic Determination of Left Ventricular Volume," *ACTA Radiologica*, vol. 56, Nov. 1961, pp. 321–339.

*Primary Examiner*—William E. Kamm

[57] ABSTRACT

A left ventricular assist device consisting of a balloon inflated and deflated sequentially to coincide with ventricular systole and diastole, respectively, placed within the left ventricle, thereby augmenting ejection of blood.

8 Claims, 18 Drawing Figures

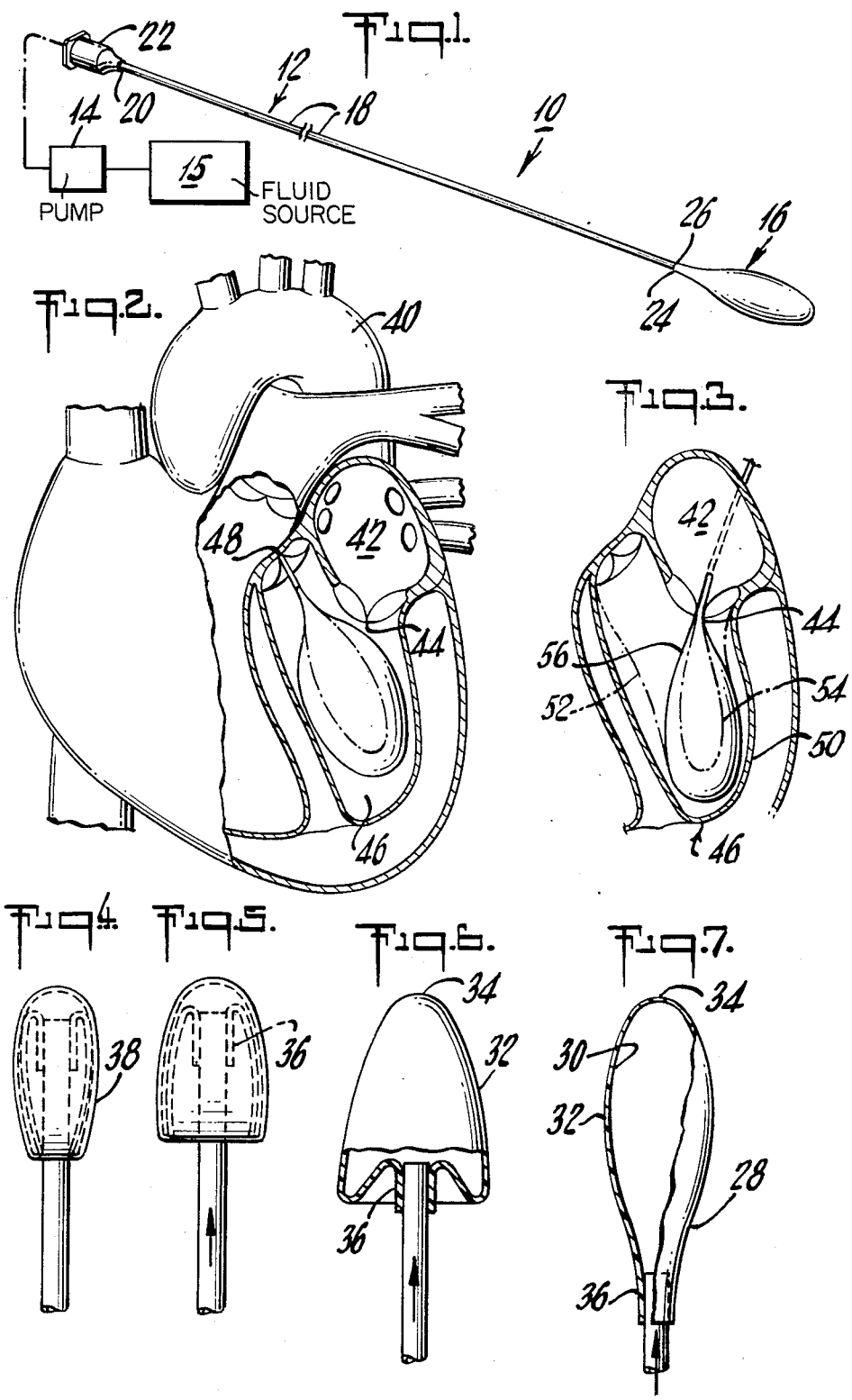

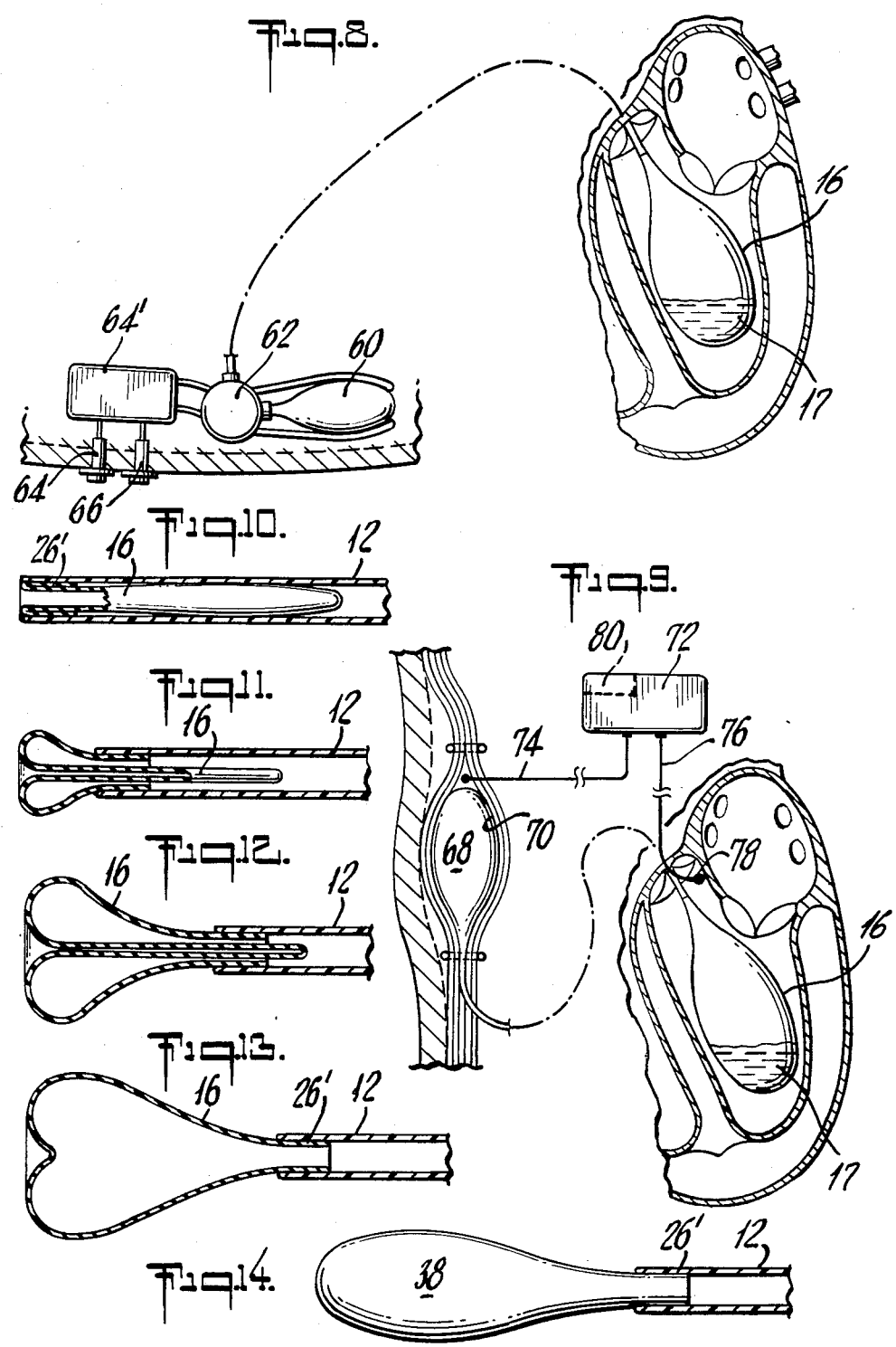

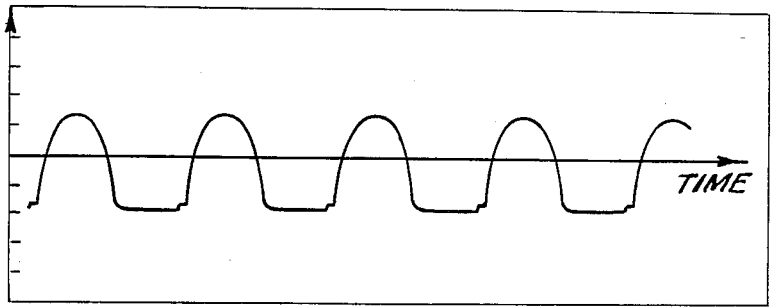

METHOD FOR USING A VENTRICULAR ASSIST DEVICE

BACKGROUND OF THE INVENTION

The present invention relates to a method for using a ventricular assist device, and more specifically is directed to a device in which the expandable member is placed directly within the left ventricle of the heart to facilitate complete ejection of the blood during systole.

In certain pathological conditions the heart, and principally the left ventricle, cannot contract fully during systole, so there is incomplete emptying of the heart. The amount of blood left in the ventricle at the end of systole is the "dead volume or space" and represents unused pumping capacity.

Damage to the left ventricular muscle arises from a variety of causes, whether chemical, physical, bacterial and viral, and leads to decrease of contractility and therefore a decrease of ejection fraction. Congestive heart failure results which may be correctable to varying degrees by pharmacological or mechanical intervention.

In intractable left ventricle failure, when it is not possible to increase the stroke volume, the "dead volume or space" is left at the end of the systole.

The prior art devices appear generally to be in the nature of U.S. Pat. No. 3,266,487 which consists of devices which are placed within the aorta. None of the devices are placed directly within the left ventricle where they can operate more efficiently. U.S. Pat. No. 3,592,183 is a ventricular assist device having an aortic balloon with a somewhat similar shape to that of the present invention, but it does not perform the same functions and it is not positioned within the left ventricle.

It is therefore an object of the present invention to provide a method for using a ventricular assist device which is designed to restore normal stroke volume.

Still yet another object of the present invention is to provide a method for using a device which restores normal stroke volume by obliterating the dead volume or space in a damaged left ventricle.

Still yet another object of the present invention is to provide a method for using a device which is inserted directly into the left ventricle and operates with greater efficiency than prior art devices.

Yet a further object of the present invention is to provide a method for using a device which may be implanted within the body of the user and is not tethered to any external operating elements.

Still yet a further object of the present invention is to provide a method for using a device which only requires connection to an external electrical source.

Still yet another object of the present invention is to provide a method for using a device which will be easy to insert and yet be capable of operating at high efficiency.

Still yet a further object of the invention is to provide a method for using a device which will be simple and economical to manufacture and yet be durable to a high degree during the time of use required by the patient.

BRIEF DESCRIPTION OF THE INVENTION

The invention is a method for using a ventricular assist device having a catheter with a proximal end and a distal end, a pump secured to the proximal end of the catheter, and an inflatable balloon secured to the distal end of the catheter. The balloon is inserted into the left ventricle of a patient's heart. The balloon is inflated during left ventricular systole, and then the balloon is deflated. The inflating and deflating steps are repeated. Preferably, the inflating step starts at approximately the beginning of left ventricular systole and stops at approximately the end of left ventricular systole. The balloon may be inserted into the heart through the mitral valve, through the aortic valve, or through the apex of the left ventricle. The pump is advantageously implanted within the patient's body, e.g., within an envelope of skeletal muscle.

The ventricular assist device may include a shaped radioopaque balloon connected to the tip of an intra-arterial catheter with a single lumen. The proximal end of the catheter is connected to a gas pump that is capable of inflating and deflating the balloon in a range of 50 to 120 cycles per minute. The gas used is either carbon dioxide or helium. The pump mechanism is triggered by an electronic relay connected to an electrocardiograph, so that inflation and deflation are governed by specific time sequences in the EKG corresponding to electrical systole and diastole.

The balloon is selected to properly fit within the left ventricular chamber, and is made to inflate just as mechanical systole begins. The cessation of inflation corresponds to the end of mechanical systole. Active contraction of the balloon begins at the onset of mechanical diastole. The negative pressure thus generated increases the pressure gradient between the left atrium and left ventricle, thus augmenting diastolic filling. This sequence of events enables the balloon to expand meeting the incoming (contracting) walls of the ventricle, thus obliterating the dead space and augmenting stroke volume. Since the Mitral valve is closed, and the Aortic valve is open, all the blood ejected flows distally into the aorta in a physiologic manner.

While it is possible to operate the ventricular assist device by means of external manipulation as is done in prior art devices, it is preferred to have the device wholly implanted within the body of the user, requiring no external equipment for proper operation. This is possible by creating a muscle pump, for example, by using skeletal muscle with timed means to internally stimulate the muscle causing appropriate inflation and deflation of the balloon. Another modified embodiment uses a solenoid pump with contacts lying just on the outer surface of the skin, designed to be connected to an external power source. Thus, the unit can be either self-contained and has a "no tether" feature or a "no tubetether" feature.

The above description, as well as further objects and advantages of the present invention will be more fully appreciated with reference to the following detailed description of a preferred, but nonetheless illustrative embodiment of the invention, when taken in conjunction with the following drawings, wherein:

FIG. 1 is a front perspective view of an improved ventricular assist device;

FIG. 2 is a view of the heart showing the device in a temporary installation passing through the Aortic valve in its inflated state in solid line and in its deflated state in dotted line.

FIG. 3 is a view similar to FIG. 2, but primarily of the left ventricle showing the device in a permanent installation passing through the Mitral valve in its inflated state in solid line and in its deflated state in dotted line.

FIG. 4 is a view showing the balloon in the collapsed configuration folded back along the catheter for insertion;

FIG. 5 is a view similar to FIG. 4 with the balloon partially inflated, to the operating and inflated position;

FIG. 6 is a view similar to FIG. 5 with the balloon further inflated;

FIG. 7 shows the balloon at the distal end of the catheter in its operating, fully inflated state;

FIG. 8 is a schematic view of a structure permanently implanted in subcutaneous fat but with external electrical contacts;

FIG. 9 is a schematic view of another structure completely permanently implanted in the subcutaneous fat;

FIGS. 10, 11, 12, 13 and 14 are views of the balloon packaged in another manner to facilitate insertion via an artery or through the left atrium, from the deflated state, and with inflation, gradually extending itself beyond the end of the catheter;

FIG. 15 is a graph illustrating Aortic flow;

FIG. 16 is graph illustrating intraventricular pressure;

DETAILED DESCRIPTION OF THE INVENTION

Figure 17:
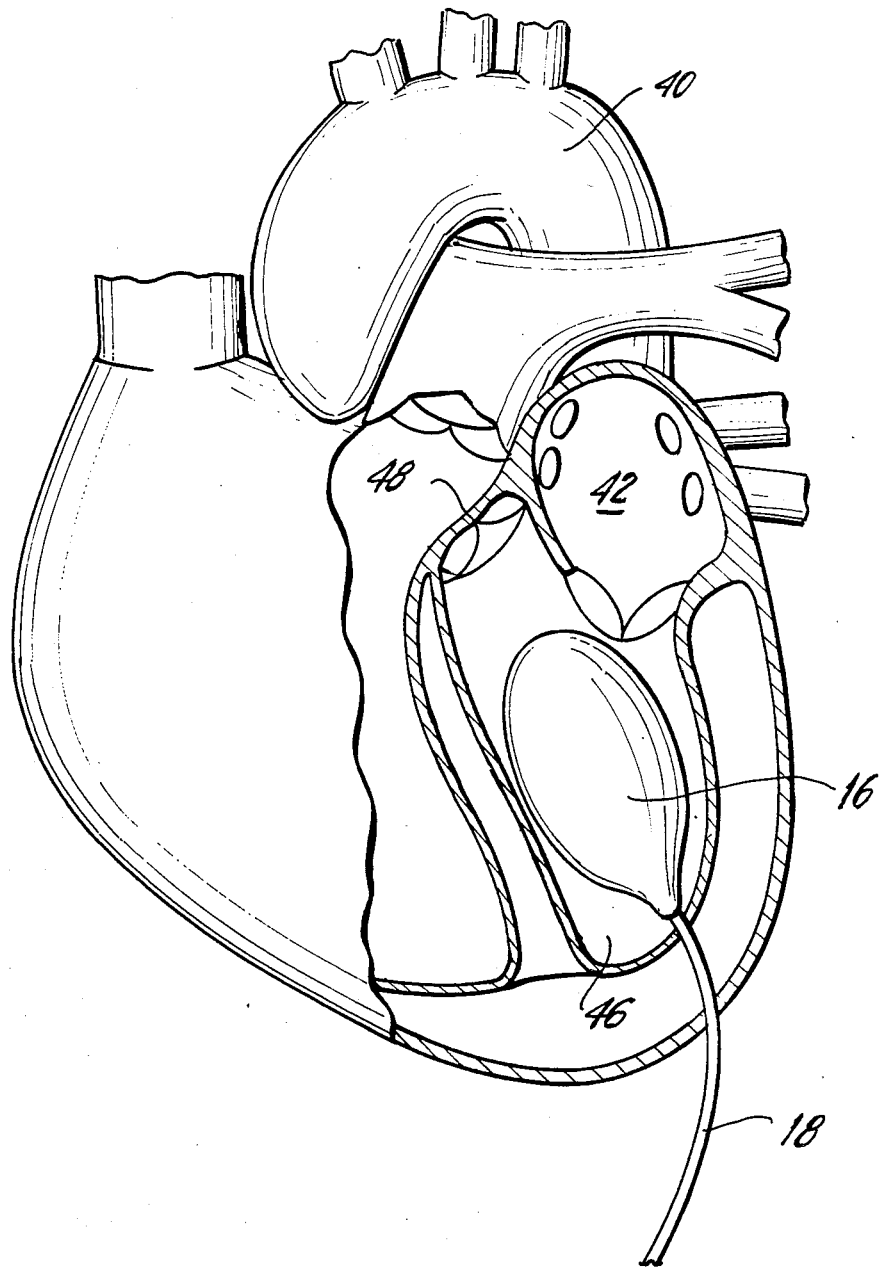
FIG. 17 is a view similar to FIG. 2 but shows a ventricular assist device inserted into the left ventricle through the apex of the left ventricle.

Referring to the drawings, and in particular to FIG. 1, there is shown an improved ventricular assist device 10 broadly comprising a catheter 12, a pump 14 (shown in schematic), a fluid source 15, and an inflatable balloon 16.

The catheter is generally made of plastic or a woven synthetic material and is a standard flexible hollow catheter defined by an outer surface 18, a proximal end 20 to which is secured an attachment member 22 for making a connection to the pump 14, and a distal end 24 having either a securement device or bonding means 26. The bonding means 26 is used to secure the balloon 16 to the distal end 24.

Turning more particularly to FIG. 7, the balloon includes a wall 28 defined by an inner surface 30 and an outer surface 32. For percutaneous insertion through a dilator: the balloon is folded so that it overlaps itself forming a crown 38 as in FIG. 4. Alternatively, it may be packaged inverted on itself inside the lumen of the catheter as in FIG. 10. Both configurations are to provide a minimal cross-sectional area to facilitate insertion. The balloon is securely attached to the distal end 24 of the catheter 18 by bonding 26, for example, as at 36 to provide an air-tight seal between the neck of the balloon and the catheter. FIGS. 5 and 6 illustrate the balloon during progressive stage of inflation.

The pump unit 14 is similar to existing pumps used to drive intra-aortic balloon assist devices and is activated at specific points in the cardiac cycle.

FIG. 2 shows a representation of the heart with the aorta 40 leading away from the opposite side of the left atrium 42. The left atrium ends at the Mitral Valve 44 which then leads into the left ventricle 46. The Aortic Valve 48 provides the exit from the left ventricle.

Turning to FIG. 3, there is shown a representation of the operation of the present invention. The outer solid line shows the maximum diastolic margin 50 of the inner ventricular wall and the maximum end systolic margin is shown in dotted line 52. The inflated balloon is shown in solid line 56 and the deflated balloon is shown in dotted line 54. The installation through the Mitral Valve as shown in this figure is a permanent installation as opposed to a temporary installation through the Aortic Valve illustrated in FIG. 2. A permanent installation may also be accomplished by inserting the balloon through the apex of the left ventricle, as shown in FIG. 17.

In order to use the present invention, the end-systolic volume and shape of the left ventricle is determined by imaging techniques, such as two-dimensional echocardiography or isotope tomography.

For example, techniques for determining left ventricular volume are disclosed in an article entitled "Usefulness and Limitations of Radiographic Methods for Determining Left Ventricular Volume," by H. T. Dodge, H. Sandler, W. A. Baxley, and R. R. Hawley, which was published in *The American Journal of Cardiology*, Volume 18, July 1966, at pages 10–24. An article entitled "The Architecture of the Heart in Systole and Diastole," by J. Ross, Jr., E. H. Sonnenblick, J. W. Covell, G. A. Kaiser, and D. Spiro, which was published in *Circulation Research*, Volume XXI, No. 4, October 1967, at pages 409–412, and an article entitled "Angiocardiographic Determination of Left Ventricular Volume," by H. Arvidsson, which was published in *ACTA Radiologica*, Volume 56, November 1961, at pages 321–339, also describe methods for measuring left ventricular volume. A preformed balloon that is just smaller than this chamber size and shape is selected. The balloon device is deflated and allowed to completely collapse as shown in FIG. 4 with the overlapping portions folded over the distal end 24 of the catheter 18. A guide wire is inserted into the femoral artery via a needle, and the needle is withdrawn. A series of increasingly larger cannulas are inserted over the guide wire until a final cannula large enough to admit the folded balloon-catheter tip combination is left in place and the balloon catheter inserted and threaded retrograde, through the Aortic Valve and into the left ventricle. To achieve neutral buoyancy at maximal inflation, an appropriate amount of mercury is introduced via the catheter into the balloon. FIGS. 8 and 9 each illustrate the balloon 16 containing mercury 17. The cannula is then removed. The proximal end 20 of the catheter is connected to the pump 14, which is then activated by an EKG monitoring the patient, so that inflation of the balloon begins with the onset of the left ventricular systole, and is completed at the end of systole. Balloon deflation coincides with the onset of ventricular diastole. In other words, inflation of the balloon occurs during the ventricular systolic interval and deflation occurs during diastole.

The volume of carbon dioxide or helium to be pumped in and exhausted will be determined by assessment of the "dead volume or space" at the end of systole. Various existing techniques, such as ultrasound imaging, or gated isotope scanning may be used to arrive at this volume. The pump will be set so the fully inflated balloon will completely fill the "dead volume".

This will eliminate the intra-ventricular dead volume created by incomplete systolic contraction of the ventricle. Since Mitral Valve closure and Aortic Valve opening mandate unidirectional flow, this "dead volume" of blood is ejected into the ascending aorta by the kinetic energy of the expanding balloon, and adds to the total ejection volume. It further facilitates diastolic filling of the left ventricle by increasing the negative pressure in the ventricle as the balloon is actively deflated.

The entire sequence described above is repeated with the end of diastole and the beginning of systole.

When used as a permanent "artifical heart", the balloon is implanted through open heart surgery with the route of entry through the left artrium, so that the catheter traverses the Mitral Valve. As stated previously, it can also be inserted through a small incision in the apex. The catheter is led out through the chest wall and connected to the pump which, of course, is extracorporeal.

FIG. 10 illustrates a modified construction for positioning of the deflated balloon 16 within the catheter 12 during insertion. The largest external diameter during insertion is that of the catheter, while in the construction shown in FIG. 4 the diameter extends to the outer surface 38 of the deflated balloon. The balloon is secured to the inner wall as at 26'. FIGS. 11-13 show the balloon during progressive stages of inflation, and FIG. 14 illustrates the fully inflated balloon.

FIG. 8 illustrates a modified construction in which the entire device, except for the power leads, are implanted subcutaneously. The balloon 16 is connected to a gas reservoir 60 which may be implanted in the abdominal fat and which is surrounded by a solenoid activated electromagnetic bellows-type pump 62. The unit is activated by a control unit 64' which senses the cardiac electrical cycle. Wires 64, 66 extend through the skin and can be connected to an external power pack (not shown) which may be carried by the patient in a shoulder holster (not shown).

FIG. 9 illustrates another modified construction which is self-contained under the skin of a patient. The balloon 16 is attached to a reservoir 68 positioned within an envelope 70 of skeletal muscle, constructed from either the pectoral or the anterior rectus muscles of the abdomen. This "envelope" or "muscle pump" is paced by a control relay 72 electrically connected by leads 74, 76 to the envelope 70 and the Sinus Node 78 of the heart or the muscle pump may be activated by a standard pacemaker. The relay is powered by a long-life Lithium battery 80. The relay is activated by the Sinus Node and initiates contraction of the muscle pump at the onset of mechanical systole, and relaxation at the onset of diastole.

The balloon 16 used in the construction of FIGS. 8 and 9 is made of thicker material than the reservoirs 60, 68 so that it will normally deflate, thereby inflating the reservoirs.

Figure 18:
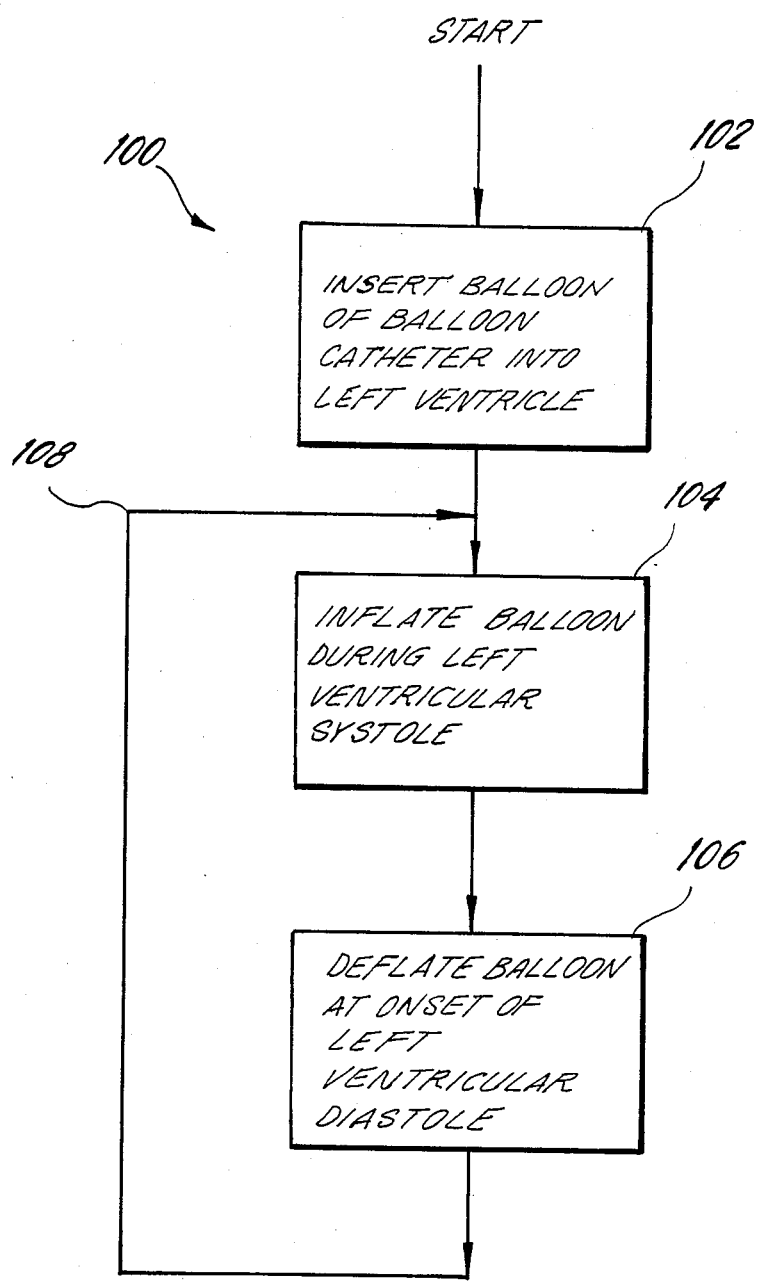
FIG. 18 is a flow chart illustrating a method according to the invention.

FIG. 18 is a flow chart showing a method according to the invention. The flow chart, which is generally designated by the reference numeral 100, contains a number of blocks. Each block represents a different step of the method. A balloon catheter is inserted into the left ventricle of a patient's heart (block 102). The balloon is inflated during left ventricular systole (block 104), and the balloon is deflated during left ventricular diastole (block 106). Then, the inflating and deflating steps are repeated, as indicated by the line 108.

SUPPLEMENTARY DATA

The ventricular assist device as described above has been tested in vitro and in vivo.

In Vitro

In the vitro system, an artificial circulatory system was constructed consisting of
(1) a clear plexiglass chamber (left ventricle),
(2) an inlet port with a one way valve (Mitral Valve),
(3) an outlet port (aorta) with a one way (Aortic Valve),
(4) plastic tubing leading from the outlet port to an air damper, and
(5) plastic tubing leading from the air damper to the inlet port.

Through an air tight seal the balloon was inserted into the chamber-ventricle. A pressure transducer was placed in the chamber to measure "intraventricular pressure." An electromagnetic flow meter was placed around the exit port (aorta). The balloon was connected to a 50 ml syringe. The circulatory system was filled with saline. The balloon was alternately inflated and deflated with air to a volume of 40 ml at a rate of 24 times per minute.

Results are shown on the graphs depicted in FIGS. 15 and 16. An intraventricular pressure of 100 mm Hg and an aortic flow of 1500 ml per minute were generated.

In Vivo

A 20 kg mongrel dog was anesthetized and the heart exposed with a thoracotomy. Respiration was maintained through an endotracheal tube with a respirator. A 0.5 cm incision was made in the apex of the left ventricle and the VAD inserted into the ventricle. The heart was arrested in diastole with an IV infusion of 10% KCl. The balloon was activated by hand pumping with a 50 ml syringe to a volume of 40 ml at 25 cycles per minute. This was continued for 15 minutes during which time respiration was maintained with the respirator and the heart action was totally stopped. At the end of 15 minutes, balloon assist was stopped. It was possible then to restore normal cardiac contraction by manual cardiac massage.

The implication of this experiment is that had coronary perfusion not been maintained during the 15 minutes of balloon assist, it would have been impossible to restart the heart. Obviously, then, the balloon VAD was effective in maintaining coronary flow sufficient to keep the myocardium alive and responsive to cardiac massage resuscitation. The strong implication is that normal cardiac output was maintained although the ventricle was completely stopped.

Aortic pressure during this experiment was 200/0. Aortic flow was measured with a Doppler sensor, so no absolute values are available.

As can be seen, the present invention provides a significant advance over the present state of technology. As numerous additions, modification and constructions can be performed within the scope of the invention, such scope is to be measured by the claims herein.

What is claimed is:

1. A method for using a ventricular assist device having a catheter with a proximal end and a distal end, a pump secured to the proximal end, and an inflatable balloon secured to the distal end, the pump being capable of inflating the balloon, comprising the steps of:
   pushing the balloon through a mitral valve into the left ventricle of a patient's heart;
   inflating the balloon during left ventricular systole with the catheter extending through the mitral valve;
   deflating the balloon during left ventricular diastole with the catheter extending through the mitral valve; and
   repeating the inflating and deflating steps.

2. A method for using a ventricular assist device having a catheter with a proximal end and a distal end, a pump secured to the proximal end, and an inflatable balloon secured to the distal end, the pump being capable of inflating the balloon, comprising the steps of:
   pushing the balloon through an aortic valve into the left ventricle of a patient's heart;
   inflating the balloon during left ventricular systole with the catheter extending through the aortic valve;
   deflating the balloon during left ventricular diastole with the catheter extending through the aortic valve; and
   repeating the inflating and deflating steps.

3. A method for using a ventricular assist device having a catheter with a proximal end and a distal end, a pump secured to the proximal end, and an inflatable balloon secured to the distal end, the pump being capable of inflating the balloon, comprising the steps of:
   implanting the pump within an envelope of skeletal muscle within the patient's body;
   implanting the catheter within the patient's body;
   inserting the balloon into a left ventricle of the patient's heart;
   inflating the balloon during left ventricular systole;
   deflating the balloon during left ventricular diastole; and
   repeating the inflating and deflating steps.

4. A method as recited in claim 3 further comprising the steps of:
   sensing the cardiac electrical cycle; and
   stimulating the muscle based upon the cardiac electrical cycle.

5. A method as recited in claim 4, wherein the sensing step includes sensing the cardiac electrical cycle at a sinus node of the patient.

6. A method for using a ventricular assist device having a catheter with a proximal end and a distal end, a pump secured to the proximal end, and an inflatable balloon secured to the distal end, the pump being capable of inflating the balloon, comprising the steps of:
   determining a maximum end systolic margin of the left ventricle of the patient's heart;
   sizing the balloon so that the balloon is smaller than the maximum end systolic margin;
   inserting the balloon into the left ventricle of the patient's heart;
   inflating the balloon during left ventricular systole;
   deflating the balloon during left ventricular diastole; and
   repeating the inflating and deflating steps.

7. A method for using a ventricular assist device having a catheter with a proximal end and a distal end, a pump secured to the proximal end, and an inflatable balloon secured to the distal end, the pump being capable of inflating the balloon, comprising the steps of:
   determining a dead volume at the end of left ventricular systole;
   inserting the balloon into a left ventricle of the patient's heart;
   inflating the balloon during left ventricular systole to completely fill the dead volume;
   deflating the balloon during left ventricular diastole; and
   repeating the inflating and deflating steps.

8. A method for using a ventricular assist device having a catheter with a proximal end and a distal end, a pump secured to the proximal end, and an inflatable balloon secured to the distal end, the pump being capable of inflating the balloon, comprising the steps of:
   inserting the balloon into a left ventricle of the patient's heart;
   introducing mercury into the balloon through the catheter to achieve neutral bouyancy at maximal inflation;
   inflating the balloon during left ventricular systole;
   deflating the balloon during left ventricular diastole; and
   repeating the inflating and deflating steps.

* * * * *